United States Patent
Bowen-Leaver et al.

(10) Patent No.: US 7,153,516 B2
(45) Date of Patent: Dec. 26, 2006

(54) RINGING NANOGEL COMPOSITIONS

(75) Inventors: Heather A. Bowen-Leaver, Lindenhurst, NY (US); Charles Craig Tadlock, Islip Terrace, NY (US); Liliana George, Centerport, NY (US)

(73) Assignee: Color Access, Inc., Melville, NY (US)

( * ) Notice: Subject to any disclaimer, the term of this patent is extended or adjusted under 35 U.S.C. 154(b) by 0 days.

(21) Appl. No.: 09/897,871

(22) Filed: Jul. 2, 2001

(65) Prior Publication Data

US 2003/0012759 A1   Jan. 16, 2003

(51) Int. Cl.
    *A61K 6/00*   (2006.01)
(52) U.S. Cl. .................. 424/401; 514/944; 514/844
(58) Field of Classification Search ............... 424/401; 514/944, 937, 938
    See application file for complete search history.

(56) References Cited

U.S. PATENT DOCUMENTS

| | | | |
|---|---|---|---|
| 4,026,818 A | | 5/1977 | Claudelli |
| 4,772,427 A | * | 9/1988 | Dawson et al. ............. 252/559 |
| 5,152,923 A | | 10/1992 | Weder et al. |
| 5,162,377 A | * | 11/1992 | Kakoki et al. ............... 514/772 |
| 5,753,241 A | | 5/1998 | Ribier et al. |
| 6,045,781 A | * | 4/2000 | Bungard et al. ............. 424/59 |
| 6,120,778 A | | 9/2000 | Simonnet |
| 6,468,551 B1 | * | 10/2002 | Diec et al. |
| 2002/0034489 A1 | * | 3/2002 | Wiegland et al. .......... 424/70.24 |

OTHER PUBLICATIONS

Sonneville-Aubrun, et al., "Oil-in-Water Nanoemulsions: A new Type of Gallenic System", XXIth IFSCC International Congress 2000, Berlin—Proceedings (6 pages).

* cited by examiner

Primary Examiner—Sreeni Padmanabhan
Assistant Examiner—Gina C. Yu
(74) Attorney, Agent, or Firm—Dorene Price

(57) ABSTRACT

The present invention relates to a method of making a ringing nanogel with low levels of emulsifiers. The oil-in-water nanogel is thickened by an oil phase and a silicone component that self-structure to increase the complex viscosity of the composition and form the nanogel. The pre-emulsion, containing the silicone component, the oil phase and a water phase, is subjected to a high shear and high pressure treatment at least two consecutive times. The self-thickening of the gel occurs when the silicone component and the oil phase provide structure to the composition. Alternatively, the silicone component can be added to a pre-emulsion of the oil and water phases after the two phases are subjected to high shear and high pressure treatment. The combination of the silicone component with the treated intermediary emulsion is subjected to a second high shear and high pressure treatment which results in self-structuring of the silicone component and the oil phase. The resulting ringing nanogel has a difference in complex viscosity of at least about 10,000 poise under oscillation stress in the range of about 0 to 5,000 (dyne/cm$^2$), and has an initial complex viscosity greater than about 15,000 poise.

13 Claims, 2 Drawing Sheets

RINGING NANOGEL COMPOSITIONS

FIELD OF THE INVENTION

The invention relates to a composition comprising a ringing gel product. More specifically, the invention relates to gelled cosmetic products comprising an oil-in-water emulsion that contains a self-structuring nanonetwork that thickens the composition and supports a vibration phenomenon associated with ringing gels.

BACKGROUND OF THE INVENTION

A "ringing" gel is a specific type of gel, so designated because it has a firm jelly-like consistency that vibrates and returns to its original configuration when lightly tapped. The vibration can be felt with the hand when the container is held and tapped, and produces a bell-like resonance. This phenomenon is believed to be due to the entrapment of oil droplets, less than about 100 nm, within the nano-network structure of the gel. It has been suggested in U.S. Pat. No. 4,026,818 that the network consists of a rod-like lamellar structure connecting dispersed particles because this type of network allows the dispersed particles to vibrate within the gel, in a manner similar to the way a ball bounces off of the internal walls of a box containing a medium or a matrix.

Clear gel products are appealing and attractive to consumers. The wet appearance (i.e., like water) of clear gels makes it easy to believe that when applied, they in fact will feel the same way—refreshing, like a splash of water. Therefore, transparency of the clear gel is an important feature. It is also desirable for the feel of a clear gel to resemble water, and especially to feel like water when it is applied to the skin. Thus, the feel of the gel is also very important.

In general, gels are shear thinning materials composed of highly viscous materials. They tend to spread easily when force is applied to them. They have varying degrees of flowability when they sit for a long period of time. The term "gel" is defined as a semisolid colloid having one dispersing component that is a fluid. The dispersion fluid can be, for example, water which is present in a considerable quantity, usually greater than about 60 percent. A colloidal solution with water as the dispersion medium is known as a "hydrosol." The aqueous system is usually thickened with agents such as acrylic polymers or gums to form the gel.

Specifically, ringing gels can be microemulsions or nanoemulsions. The microemulsion clear gel has an oil droplet particle size of about 0.01 to 0.08 microns and contains oil, water, and a high level of surfactants. The particle size of the oil droplet is small enough to allow light to pass through and create a translucent ringing gel. Conventional microemulsions are highly concentrated tenside-cotenside mixtures that achieve a minimum surface tension to stabilize the emulsion. The microemulsion is considered to be a transparent solution of micelles. The oil is dispersed in the network structure by surfactants, cosurfactants, and emulsifiers. The drawback to this system is that gels containing these ingredients can be irritating and feel sticky when applied to the skin.

Unlike microemulsions, nanoemulsions are metastable systems. Nanoemulsions comprise oil globules that have a mean particle size of less than 100 nanometers (nm). They have an appearance similar to water, and are known to feel like cream or milk. The nanoemulsion is a true emulsion because the oil droplets are dispersed in an aqueous phase.

The structure of a nanoemulsion is dependent on the process used. Some examples of processes, include, PIT (phase inversion temperature) method or spontaneous emulsification or use of a high shear device. For example, it is described in U.S. Pat. Nos. 6,120,778, 5,753,241, and 5,152,923, incorporated herein by reference, to achieve a reduction in oil droplet size with the use of a high-pressure or high shear homogenizer. The fragile nature of nanoemulsions is believed to be related to the type of oil used, and the addition of polymers to thicken or to gel the nanoemulsion. Even when using high shear homogenizers, thickeners and surfactants are still necessary in the nanoemulsion formulation to aid in the thickening of the gel. They act at the interface of the oil and aqueous phase to support the nano-network structure of the gel. The physical conditions for a stable emulsion are maximum specific interface and maximum interficial energy of the particles.

In addition to certain physical conditions, the type of oil is also known to alter the integrity of a nanoemulsion. For example, in a publication entitled "Oil-in-Water Nanoemulsions: A new Type of Gallenic System", XXIth IFSCC International Congress 2000, Berlin —Proceedings, by Sonneville-Aubrun et al., ("O/W Nanoemulsion Proceedings") one of the major sources of instability in a nanoemulsion system is the nature of the oil and the addition of polymers to thicken or to gel the nanoemulsion. Thus, there remains a need to thicken compositions without incurring the drawbacks experienced with traditional thickeners, gelling agents, and emulsifiers. The present invention provides a stable emulsion while reducing the amount of surfactants, thickeners and emulsifier traditionally used to achieve the ringing nanogel composition.

SUMMARY OF THE INVENTION

The present invention relates to a ringing nanogel composition that is substantially free of emulsifiers. The amount of emulsifiers used in the invention are substantially less than the amounts normally used to make the nanoemulsion into a ringing gel. The nanogel of the present invention is made by subjecting a water phase, an oil phase, and a silicone component to a series of high shear and high pressure ("high shear/pressure") treatments. The oil phase and the silicone component self-structure as a result of the high shear/pressure treatments. The self-structuring of the oil phase and the silicone component thickens the composition and makes a nanogel. Alternatively, the pre-emulsion can be processed with high shear/pressure treatment before adding the silicone component. After treating the pre-emulsion, the silicone component is added separately and the combination is subjected to a second high shear/high pressure treatment. The oil droplet size of the pre-emulsion is reduced by passing it through a high shear/high pressure device at least two times. The silicone component can also be added after the pre-emulsion is treated, and the combination is passed at least once more through the high shearing/pressure device. The nanogel of the present invention achieves a complex viscosity of at least about 15,000 poise while containing less than about 5 percent emulsifiers.

The method of making the present invention involves preparing an oil-in-water pre-emulsion, combining it with the silicone component, and treating it in the high shear/pressure device at least two times to form the nanogel. Alternatively, an oil-in-water intermediary emulsion is prepared by separately treating it in the high shear/pressure device before the silicone component is added to it. Subsequently, the combination is subjected to high shear/pressure at least once. The nanoemulsion is transformed into a ringing nanogel.

DETAILED DESCRIPTION OF THE INVENTION

The ability to thicken a nanoemulsion to form a ringing nanogel without using traditional cosmetic emulsifiers is surprising because emulsifiers are known to be necessary to add structure to a composition and hence create a gel. The physical presence of a thickener, gelling agent, emulsifier, or even a surfactant causes structure building between molecules in the composition, typically the dispersed oil droplets, and the viscosity of the composition increases. However, many agents used to increase viscosity also interfere with the transparency of the gel. Therefore, achieving the fine balance between thickening the gel and maintaining its clarity is a challenge. As reported in O/W Nanoemulsions Proceedings, nanoemulsions are metastable systems which, because of their transparency, reveal even the slightest hint of destabilization by appearing opaque or creamy. Therefore, many attempts have been made to increase the viscosity of these gels without compromising the clarity of the gel.

In one example of fine-tuning the balance between thickening and gelling, a non-ionic amphiphilic lipid component of polyethylene glycol, sorbitan, glycerol, or polyglycerol is used in U.S. Pat. No. 5,753,241, and in U.S. Pat. No. 6,120,778, a silicone surfactant is used. However, because of the reliance on surfactants these compositions can be irritating to the skin. Further, gelling agents are added to the fluid compositions to thicken them into a gel. In another example, ringing gels disclosed in U.S. Pat. 4,026,818 use 5 to 9 percent by weight of a Kritchevsky type base and isostearic acid as components to thicken the microemulsion. This allegedly reduces the tackiness and defatting of the gel. However, the use of the acid base component to gel the system is undesirable because it relies primarily on a soap-based gellant, high levels of which can be drying to the skin. However, the ringing nanogels of the present invention are achieved without using large quantities of traditional emulsifiers to thicken the gels.

The resulting nanogels of the present invention feel pleasant on the skin and have excellent clarity without using a substantial amount of thickening agents, as such are known and described in the CTFA as Viscosity Increasing Agents—Aqueous, and—Nonaqueous, 1995 ed., incorporated herein by reference. As used herein, the term "without a substantial amount" of thickening agents means that the amount of thickening agents is less than 5.0 percent, and preferably close to zero, for example, less than 0.5 percent and includes the absence of thickening agents, altogether. The scope of the present invention includes both ringing nanogels with a small amount of emulsifiers and substantially no emulsifiers. Therefore, this definition also applies to emulsifiers.

Figure 1:
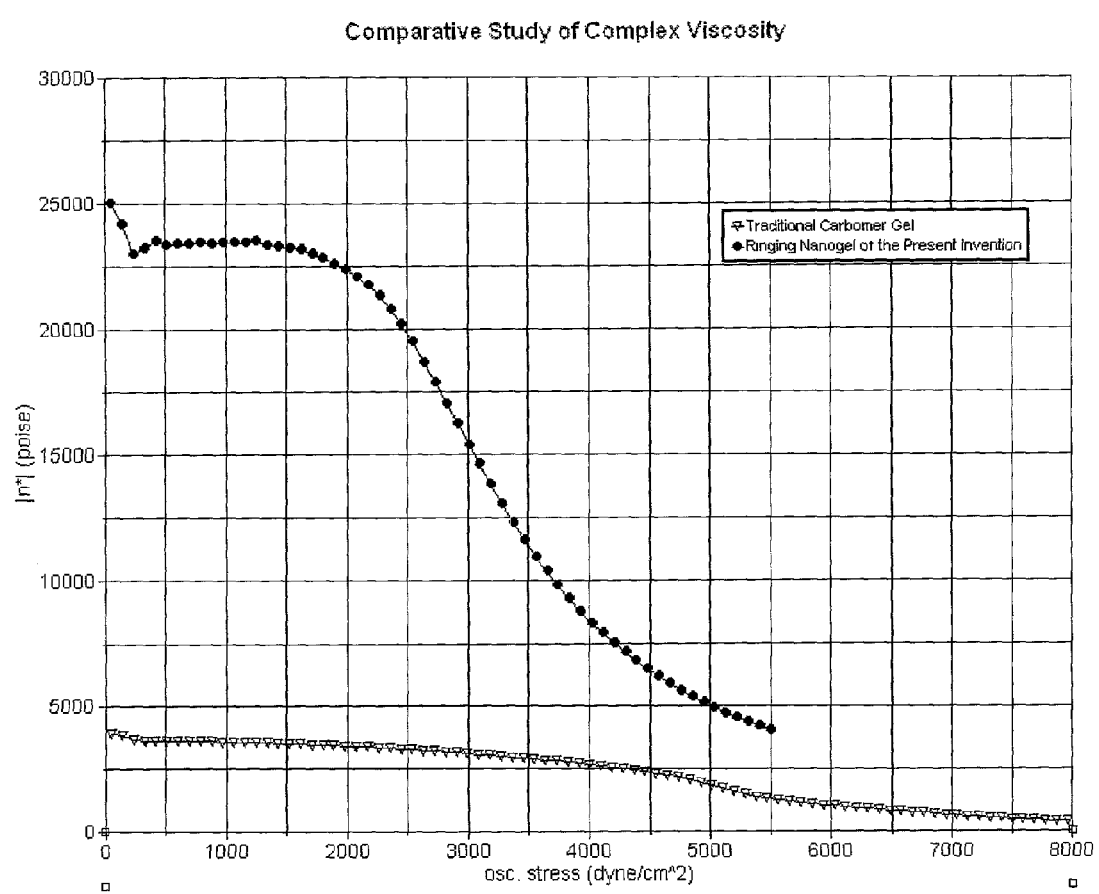
FIG. 1 is a chart entitled "Comparative Study of Complex Viscosity" which depicts the complex viscosity of a Traditional Carbomer Gel and the Ringing Nanogel of the Present Invention in units of poise over a range of oscillation stress expressed in units of dyne/cm$^2$.
Figure 2:
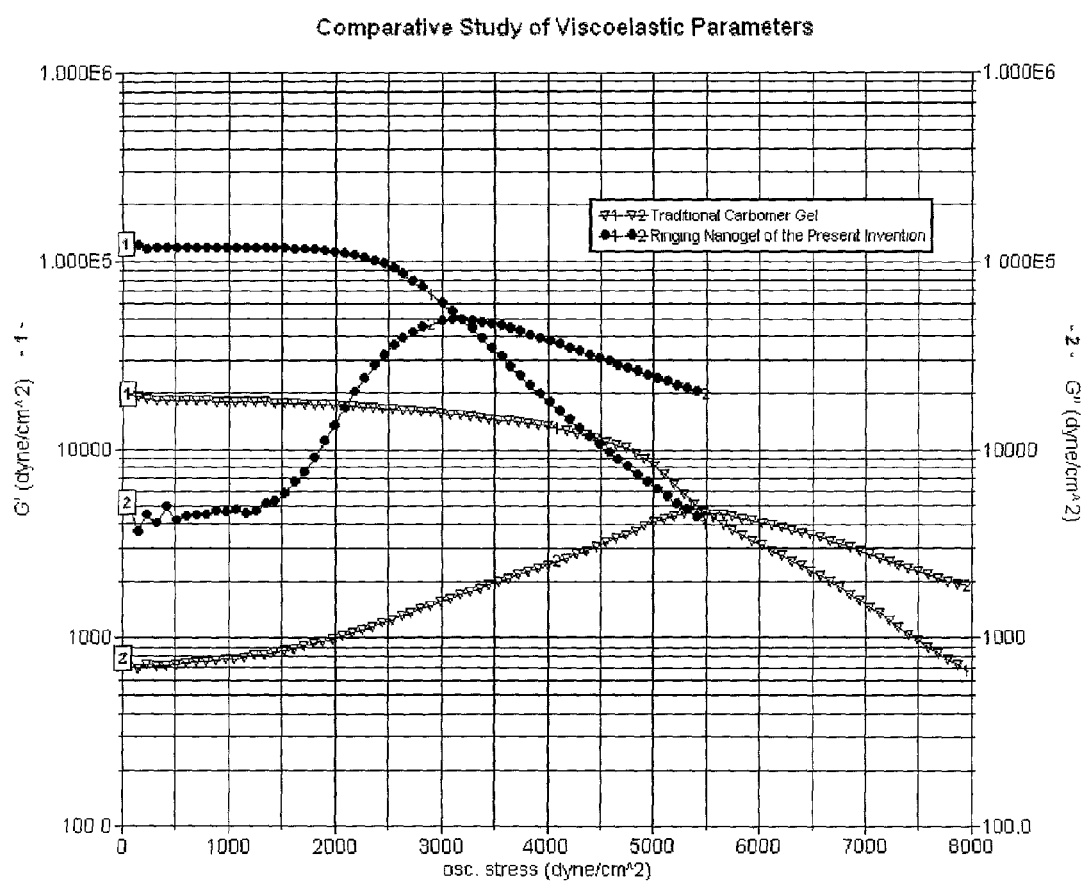
FIG. 2 is a chart entitled "Comparative Study of Viscoelastic Parameters" which depicts the viscoelastic parameters of a Traditional Carbomer Gel and the Ringing Nanogel of the Present invention in terms of G' and G" over a range of oscillation stress wherein each parameter, G', G", and oscillation stress, is expressed in units of dyne/cm$^2$.

In particular, the nanogels of the present invention, upon application to the skin, undergo a breaking phenomenon whereby the complex viscosity of the nanogel breaks down (i.e., is drastically reduced) and releases a refreshing wet feel as it is rubbed onto the skin. As indicated by FIG. 2, "Comparative Study of Viscoelastic Parameters", the ringing nanogel of the present invention has a rheological profile unlike that of a traditional gel prepared with a carbomer. The ringing nanogel of the present invention is characterized by two parameters, stiffness, G' (dyne/cm$^2$), and viscous component G" (dyne/cm$^2$). The ringing nanogel of the present invention achieves a stiffness as measured by G' that is about an order of magnitude greater than the stiffness of a traditional gel made with carbopol. When oscillation stress (dyne/cm$^2$) is greater than 2,000, the nanogel of the present invention undergoes a breaking phenomenon. The stiffness drops from a G' greater than about 100,000 to about 6,000 when the oscillation stress increases from about 2,000 to about 5,000. This phenomenon is also indicated by data in FIG. 1, "Comparative Study of Complex Viscosity", wherein the complex viscosity (poise) of the ringing nanogel of the present invention is illustrated. The difference in complex viscosity, in the oscillation stress range of 2,000 to 5,000, is at lease 15,000 poise, and preferably at least about 20,000 poise. The initial complex viscosity of the nanogel is at least about 15,000 poise. The ringing nanogel of the present invention has a viscous component, G" (dyne/cm$^2$) shown in FIG. 2, about 5,000 under oscillation stress of about 1,000. Between oscillation stress of about 1,000 to about 3,500, the G" increases from about 5,000 to about 50,000. The G' to G" crossover point occurs when oscillation stress is about 3,200, and G' and G" are both equal to about 50,000.

The traditional gel, however, basically maintains a consistent G' throughout the range of oscillation stress between about 2,000 and about 5,000 as indicated in FIG. 2 by G' which is between about 20,000 to about 8,500. This is also found when measuring the complex viscosity, as shown in FIG. 1. The initial complex viscosity (poise) is about 4,000 and drifts from about less than 5,000 to about 2,000 in the range of oscillation stress between 0 and 5,000. The difference in complex viscosity in the same range of oscillation stress is about 2,000. The viscous component, G" in FIG. 2, of the traditional gel is about 800 under oscillation stress of about 1,000, and increases to less than about 5,000 around oscillation stress of about 5,500 (i.e., G" reaches a maximum of about 5,000 around oscillation stress of about 5,500), which is also the G' to G" crossover point for the traditional gel. Thus, less pressure is required to spread the nanogel of the present invention because its G' to G" crossover point is around 3,000 oscillation stress as opposed to the crossover point of the tradition gel at about 5,500 oscillation stress. More stress must be applied to spread the traditional gel than the ringing nanogel of the present invention. Therefore, it is easier to massage the nanogel of the present invention on the surface of the skin. In addition, because of the higher complex viscosity, the sensation of the nanogel on the skin is different than the traditional carbomer gel.

The nanogel of the present invention, does not just feel smooth, or creamy. Rather, upon application the feel of the nanogel of the present invention changes from a pleasant smooth feeling to a wet-like feel. Further, the ringing nanogels prepared according to the present invention do not feel tacky upon drying like the traditional carbomer gel or microemulsion ringing gels. The present nanogels are also capable of delivering hydrophobes better than the carbomer gel because the carbomer gel system is water based. The ringing nanogels of the present invention are thickened with the self-structuring silicone component and the oil phase, and therefore, are better able to deliver hydrophobes. The ability to achieve a smooth and easy-to-spread gel that is at the same time thick in consistency is surprising, especially since it is achieved with a low level of emulsifiers or even in the absence of emulsifiers altogether.

The method of preparing the ringing nanogel of the present invention involves a first step of preparing a simple emulsion of the oil and water phases. The components of the water phase are combined, and the components of the oil phase are combined separately from the water phase. After the water phase and the oil phase are prepared the two are mixed together to make the pre-emulsion. The emulsion is combined with the silicone component using known mixing techniques and the combination is subjected to a high shear/pressure treatment. As used herein, the "high shear/pressure" treatment or device refers to a treatment or device that applies a combination of high shear and high pressure to the emulsion to form the ringing nanogel of the present invention.

In a preferred embodiment of the present invention, a pre-emulsion, containing the water and oil phases without the silicone component, is subjected to a first high shear/pressure treatment at least two separate times. The silicone component is subsequently added to the treated intermediary emulsion and the combination is subjected to a second separate high shear/pressure treatment. The first high shear/pressure treatment is applied to the original pre-emulsion of only the oil and water phases, and the pre-emulsion is passed through a high shear/pressure device at least two times. The silicone component is added to the treated intermediary emulsion, and the second high shear/pressure treatment is conducted by passing the combination at least once through the high shear/pressure device.

The high shear/pressure device, can be in the form of a homogenizer, or any other apparatus that allows the oil droplet size of the pre-emulsion to be reduced to less than about 100 nm, preferably about 30 to 75 nm, and more preferably 40 to 60 nm by a combination of high shear and high pressure. Each high shear/pressure treatment is conducted at about 10,000 to 20,000 pounds per square inch (psi). Preferably, the pressure is about 15,000 psi. Suitable high shear/pressure devices are known in the art and are commercially available products, such as, for example, Microfluidizer 110Y by Microfluidics Corp, Newton, Mass. Preferably, the pre-emulsion is treated with high shear/pressure three times before adding the silicone component. After the silicone component is added to the treated intermediary emulsion, the combination is treated with high shear/pressure at least one additional time and a nanogel is formed. The output temperature is in the range of about 30 to 45° C.; and preferably, it is room temperature, about 25° C. At cooler temperatures, the nanogel is thicker than at warmer temperatures depending on the volatility of the oils used. The oil droplets can deliver actives, especially oil soluble actives, to the skin surface. To further enhance the incorporation of actives in either of the phases, additional alcohols or glycols can be used. These additional ingredients improve the transparency of the ringing nanogel, as well as act as solubilizers. Transparency, as measured by the transmittance at a wavelength of about 600 nm, is preferably about 30 to 90 percent, and more preferably 60 to 90 percent.

The composition is thickened when the silicone component, the water phase, and the oil phase self-structure during the high shear/pressure treatment. The water phase can include water, as well as aqueous solutions of teas, broths, wines, wine yeasts or other ferments, or fish cartilage. In addition, to further increase the clarity, glycerin can be added to the water phase. Other additives to the water phase can be alcohols, glycols such as propylene glycol, 1,3-butylene glycol, dipropylene glycol, or polyethylene glycols containing from 4 to 16 oxide units. The additives in the water phase can be present in an amount between about 5 to 25 percent of the total composition.

The oil phase of the present ringing nanogel can include any type of cosmetically acceptable oil including animal or vegetable oils, natural or synthetic oils, hydrocarbon oils, or silicone oils. Preferably, the oil is non-volatile. Oily esters, such as, for example, but not limited to, isopropyl stearate, butyl stearate, octyl palmitate, cetyl palmitate, tridecyl behenate, diisopropyl adipate, dioctyl sebacate, menthyl anthranhilate, cetyl octanoate, octyl salicylate, isopropyl myristate, neopentyl glycol dicarpate cetols, or Ceraphyls™ such as for example, decyl oleate, diisopropyl adipate, $C_{12-15}$ alkyl lactates such as cetyl lactate and lauryl lactate, isostearyl neopentanoate, myristyl lactate, isocetyl stearoyl stearate, and ocyldodecyl stearoyl stearate, depending on the application of the product, can be used. Other examples include, but are not limited to, hydrocarbon oils such as, isoparaffins, fluid paraffins, squalane, isododecane, petrolatum; animal or vegetable oils, such as, for example, apricot, jojoba (simmondsia chinensis seed oil), grapeseed, macadamia, wheat germ, almond, rapeseed, gourd, soybean, sesame, hazelnut, maize, sunflower, hemp, bois, kuki nut, avocado, walnut, fish oil; fatty acids such as oleic acid, linoleic acid; fatty alcohols such as, oleyl alcohol, isostearyl alcohol; silicone derivatives, such as, methylphenylpolysiloxane; non-volatile silicones can include, but are not limited to polymeric silicone such as simethicone, dimethicone, phenyltrimethicone, any organomodified version thereof; alkylated derivatives of polymeric silicones, such as cetyl dimethicone and lauryl trimethicone; hydroxylated derivatives of polymeric silicones, such as dimethiconol; and combinations thereof. More preferably, the oil is a non-volatile hydrocarbon. Still more preferably, the hydrocarbon oil is squalane. The oil phase in the nanogel, including the silicone component, is present in an amount of at least about 20 percent; preferably, about 20 to 60 percent of the composition; more preferably, about 20 to 45 percent. Thus, the amount of the oil is high in comparison with the emulsifier, at least five times as great.

The silicone component comprises at least one volatile silicone oil. The volatile silicone oil can be the sole oil in the silicone component or it can be combined with other silicone and non-silicone oils. The other oils can be volatile or non-volatile. The volatile oil used in the silicone component is different than the oil in the oil phase. Suitable volatile silicone oils for thickening the nanoemulsion include, but are not limited to, both cyclic and linear silicones, such as cyclomethicone, and other derivatives of cyclomethicone, for example, hexamethylcyclotrisiloxane, octamethylcyclotetrasiloxane, decamethylcyclopentasiloxane, or volatile linear dimethylpolysiloxanes, and mixtures thereof. Suitable non-volatile oils that can be used are described above. If the silicone oil is combined with another volatile or non-volatile oil, the ratio of silicone oil to the other oil is from about 1:3 to 10:1. The silicone oil is preferably combined with a volatile oil, for example, a volatile hydrocarbon or another volatile silicone oil. Examples of volatile hydrocarbon include but are not limited to isohexadecane, isoeicosane, isotetracosane, polyisobutene, isooctane, and isododecane.

Preferably, the volatile silicone oil is present in an amount of about 2 to 40 percent; more preferably 10 to 35 percent by weight of the composition. Another benefit to the present invention, due to the high percentage of oil in the ringing nanogel, is a soft, silky and pleasant feeling that the gels have in comparison with gels prepared using traditional polymers, like carbomer gels, as the thickening agent. However, as previously mentioned, the nanogel breaks upon application to the skin and also provides a wet feel. In addition, the ringing nanogel of the present invention can be achieved with various water to oil phase ratios, however, the oil phase and the silicone component are at least 30 percent by weight of the composition.

Although the nanogels of the present invention can be prepared without traditional thickeners, small amounts of thickeners can be used. Examples of aqueous thickeners can include, for example, acrylates copolymer, carbomer, cellulose gum, cetearyl alcohol, cetyl alcohol, cocamide DEA, cocamide MEA, cocamide MIPA, starch, gelatin, guar gum, hectorite, hyaluronic acid, polyethylene glycol, polyvinylpyrrolidone copolymer, stearamide, and xanthan gum. Preferably, the ringing nanogels of the present invention have less than about 5 percent thickening agents; more preferably, they have less than about 1 percent; and more preferably still, they have less than about 0.5 percent all by weight of the composition. In a preferred embodiment of the present invention, the ringing nanogel is monohydric alcohol-free.

The ringing nanogels of the present invention also use less surfactants. However, a small amount of surfactants is used in the present invention. Typically the amount of surfactant is about 5 to 10 percent by weight of the nanogel composition. Suitable surfactants can be anionic, nonionic and amphoteric. Anionic surfactants include, but are not limited to, sulfates, such as linear and branched primary and secondary alkyl sulfates, alkyl ethoxysulfates, alkyl ether sulfates, fatty oleyl glycerol sulfates, alkyl phenol ethyoxylated sulfates, alkyl phenol ethylene oxide ether sulfates, C5–C16 acyl-N—(C1–C4 alkyl) and —N—(C1–C2 hydroxyalkyl) glucamine sulfates, and sulfates of alkyl polysaccharides such as the sulfates of alkyl polyglucoside; sulfonates such as salts of C5–C20 linear alkylbenzene sulfonates, alkyl ester sulfonates, C6–C22 primary or secondary alkane sulfonates, C6–C24 olefin sulfonates and alpha sulfonated C1–C6 alkyl esters of a fatty acid having an average of from about 11 to about 16 carbon atoms; carboxylates, such as alkyl ethoxy carboxylates, alkyl polyethoxy polycarboxylates surfactants, and their soaps, especially secondary soaps; sulfosuccinates such as C8–C22 sulfosuccinates; sarcosinates such as alkali metal sarcosinates; or sulfoacetates such as C12–C20 alkyl sulfoacetates, for example, lauryl and myristyl sulfoacetate in the form of their sodium salts.

Nonionic surfactants can be semi-polar including, but not limited to, water soluble amine oxides, water soluble sulfoxides having at least one C10–C18 alkyl moiety and at least one moiety selected from the group consisting of alkyl groups and hydroxyalkyl groups containing from about 1 to 3 carbon atoms, or amine-oxide derived surfactants (e.g., cocoamine oxide). Ethoxamides include, for example, ethoxylated alkanol amides or polyethylene glycol amides such as PEG-3 cocoamide or PEG-6 lauramide. Amphoteric surfactants include, but are not limited to, alkyl glycinates, propionates, imidazolines, amphoalkylsulfonates, N-alkylaminopropionic acids, N-alkyliminodipropionic acids, imidazoline carboxylates, N-alkylbetaines, amido propyl betaines, sarcosinates, cocoamphocarboxyglycinates, amine oxides, sulfobetaines, or sultaines.

The nanogels of the present invention require a minimal amount of emulsifiers to form the gel, like the surfactants as some surfactants act as emulsifiers at the interface between the oil and the water phases. Preferably, no greater than 8 percent is used; however, nanogels of the present invention can be prepared with no greater than 5 percent by weight of the composition as well as free of emulsifiers. The emulsifiers used in the gels are suitable for use in an oil-in-water emulsion. The HLB value of the emulsifier is, in general, about 8 to 18, as it is known for its suitability as an oil-in-water emulsifier. They are preferably mild and substantially non-irritating. Examples of emulsifiers can include but are not limited to fatty acids (e.g., oleic acid, linoleic acid, stearic acid, palmitic acid, and ricinoleic acid) polyoxyethylene ethers and their phosphate esters (e.g., POE (20) oleyl ether, oleth-10 phosphate, POE (20) sorbitan monooleate); polyethylene glycol, their esters of fatty acids such as stearic, lauric and oleic acid (e.g., PEG-2 stearate, PEG-100 stearate), and their ethers (e.g., PEG-10 oleyl ether, isosteareth-20); polymers such as alkylmonoesters of poly(methylvinylether/maleic acid) resins, polyoxyethylene polyoxypropylene block copolymers, polyoxybutylene-polyoxyethylene block copolymers, ethoxylated lanolin alcohols, sclerotium gum, sodium stearoyl glutamate, stearyl heptanoate; glyceryl esters such as glyceryl mono undecylenate, glyceryl stearate, and polyglyceryl-2 diisostearate; stearyl alcohol; lecithins; and carboxyl vinyl polymers. Preferably, the fatty acid is stearic acid, and the molecular weight of the polyethylene glycol ester is less than 200, preferably less than 100. The emulsifier can be added to the oil phase, the water phase or the silicone component. If it is added to the silicone component it may be a silicone surfactant such as, for example, a polyoxyalkylene modified organopolysiloxane, such as dimethicone copolyol.

The ringing nanogel of the present invention can be used in a variety of products. Examples of products include, but are not limited to, eye products, facial products, body products, lip products, nail products, hair products and any other makeup, or skin or sun care product that is suitable in a gel or gloss type product, that is substantially clear, and applied to the eye area, face, neck, hands, nails, hair or body. For example, the product can be in the form of a cleanser, make-up remover, or bath or shower gel. The products utilizing the nanogel of the present invention may also contain suspended particles that produce a unique appearance to the gel. Examples of particles, include, but are not limited to, micas, pigments, and liquid crystals. The pigments can be organic or inorganic. The organic pigment can be, for example, natural pigments, monomeric and polymeric synthetic pigments, or combinations thereof. Exemplary organic pigments include, but are not limited to, phthalocyanine blue and green pigments and azo-type red pigments such as naphthol red pigment. Other suitable aromatic pigment compounds include, but are not limited to, azo, triphenyl methane, indigo, anthraquinone, and xanthine dyes which are referred to as D&C, and FD&C pigments, such as for example, FD&C blue No. 1, FD&C green No. 5, FD&C red No. 40, FD&C red No. 7, and FD&C yellow No. 5. Also useful are lakes, which are pigments formed by the precipitation and absorption of organic dyes in an insoluble base, such as alumina, barium, or calcium hydrates. Particularly preferred lakes are primary FD&C or D&C Lakes, and blends thereof. Addition of these various pigments and colorants gives the ringing gel a unique appearance. Colorant concentrations will vary depending upon the desired color or tint of the cosmetic product, but generally will be in the range of from about 0.1 to about 10.0 percent by weight of the total composition.

The colorant can also be an inorganic pigment. The inorganic pigment is present in low amounts, and preferably, the inorganic pigment has a small particle size, for example, a submicron particle size that will disperse and permit the cosmetic product to maintain a clear appearance. Examples of inorganic pigments include, but are not limited to, iron oxides (yellow, red, brown or black), ultramarines, chromium hydroxide green, chromium oxide, titanium dioxide (white), ferric ferrocyanide, ferric ammonium ferrocyanide, and mixtures thereof.

Active ingredients in a nanogel can be contained in either the water phase or the oil phase usually depending on the solubility of the active ingredient. The nanogels of the present invention advantageously can contain active agents in the oil phase. Such actives include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antimotion sickness agents, anti-inflammatory agents, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, wound-healing agents, vitamins, corticosteroids, or hormones. More specific examples of useful active agents include topical cardiovascular agents, clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocycline, hydroquinone, minocycline, naproxen, ibuprofen, theophylline, cromolyn, albuterol, retinoids, retinoic acid, 13-cis retinoic acid, vitamin A palmitate, hydrocortisone, hydrocortisone 21-acetate, hydrocortisone 17-valerate, hydrocortisone 17-butyrate, betamethasone valerate, betamethasone diproprionate, triaminolone acetonide, fluocinonide, clobetasol, proprionate, benzoyl peroxide, crotamiton, propranolol, promethazine, tocopherol, vitamin E acetate, derivatives and mixtures thereof. The amount of active agent to be used in any given formulation is readily determined in accordance with its usual dosage, and its compatibility with the ringing nanogel.

Further, the gel of the present invention can contain other optional components as long as they do not interfere with the clarity of the nanogel. Examples include, but are not limited to, one or more preservatives such as, for example, propyl paraben, butyl paraben, methyl paraben or an isomer, homolog, analog or derivative thereof, mixtures thereof, or isoforms thereof, as well as butyl hydroxy toluene or butyl hydroxy anisol (BHT or BHA); chelating agents such as disodium ethylene diamine tetraacetic acid ("EDTA"); fragrances (such as pinene); flavoring agents; waterproofing agents (such as PVP/eicosene copolymer); and the like. High levels of fragrance oils can be added up to an amount of about 10 percent. Preservatives employed may be in an amount of from 0.01 to 2 percent, preferably from 0.01 to 1 percent, of the formula weight.

The invention is further illustrated by the following non-limiting examples.

EXAMPLE

Clear Ringing Gel

| Ingredient | % Amount |
|---|---|
| Phase I | |
| Purified water | 47.00 |
| Glycerine | 10.00 |
| Isoprene glycol | 8.00 |
| Methylparaben | 0.50 |
| Sodium stearoyl glutamate | 1.50 |
| Phase II | |
| Squalane | 12.50 |
| PEG-2 stearate | 1.00 |
| Stearyl heptanoate | 1.00 |
| Glyceryl stearate/ PEG-100 stearate | 1.50 |
| Stearic acid | 0.50 |
| Phase III | |
| Cyclomethicone | 14.00 |
| Isododecane | 2.50 |

The water phase is heated to about 65° C. The oil phase is also heated to about 80° C. Allow the oil phase to cool to a temperature of about 70° C. Add the oil phase to the water phase and emulsify. Treat the resulting emulsion in a high shearing device to a pressure of about 15,000 psi, and repeat the treatment two additional times, for a total of three treatments. After the third treatment, combine the Phase III silicone component and hydrocarbon oil with the sheared emulsion. Pass the combination through the high shearing device to produce a thick clear ringing nanogel having a complex viscosity of greater than about 20,000 poise and less than 30,000 poise. A traditional gel is prepared using about 2.5 percent Carbopol Ultrez, 0.35 percent TEA99, and water, and it has a complex viscosity of less than about 5,000 poise.

The complex viscosity of the ringing nanogel of the present invention is basically at greater than 20,000 poise and less than 30,000 poise when experiencing oscillation stress (dyne/cm$^2$) between about 0 to 2,000; whereas, the complex viscosity of the traditional ringing gel is less than 5,000 poise in the same range of oscillation stress. Upon application of oscillation stress greater than 2,000, the complex viscosity of the nanogel of the present invention decreases from about 22,500 to about 5,000 at oscillation stress of about 5,000. In comparison, the traditional carbomer gel, at oscillation stress of about 5,000, experiences a complex viscosity of less than 2,500. The complex viscosity of the traditional gel drifts, therefore, from about 5,000 to 2,500. However, the drop from 5,000 to 2,500, a difference of about 2,500 for the traditional gel, is considerably less than the difference between 22,500 to 5,000 (22,000) and demonstrates the differences in the feel of the traditional gel in comparison with the nanogel of the present invention. The ringing nanogel of the present invention feels initially smooth, and soon, thereafter undergoes a breaking phenomenon and feels wet and refreshing while still maintaining the consistency of a gel on the skin.

EXAMPLE II

Translucent Eye Gel

| Ingredient | % Amount |
| --- | --- |
| Phase I | |
| Purified water | 44.00 |
| Glycerine | 10.00 |
| Isoprene glycol | 8.00 |
| Methylparaben | 0.50 |
| Capryl glycol | 1.00 |
| Sodium stearoyl glutamate | 1.50 |
| PEG-2 stearate | 1.00 |
| Glyceryl stearate | 1.00 |
| PEG-100 stearate | 1.00 |
| Stearic acid | 0.50 |
| Isostearamidopropyl dimethylamine | 0.50 |
| Phase II | |
| Squalane | 12.50 |
| Stearyl heptanoate | 1.00 |
| Cetyl alcohol | 1.00 |
| Phase III | |
| Cyclomethicone | 14.00 |
| Isododecane | 2.50 |

The eye gel is prepared according to the procedures described for Example I.

What we claim is:

1. An oil-in-water nanogel composition comprising an oil phase having a mean droplet size of less than about 100 nm, an emulsifier, a water phase, and a silicone oil component comprising at least one volatile silicone oil different than the oil phase, wherein said oil phase and said silicone component are self-structured in the absence of a thickening agent by a high shear/pressure treatment, at least about 20 percent by weight of the composition and at least about 5 times the amount of the emulsifier and the nanogel has a difference in complex viscosity of at least about 10,000 poise under oscillation stress in the range of about 0 to 5,000 (dyne/cm$^2$).

2. The composition of claim 1 further comprising the emulsifier present in an amount no greater than about 8 percent by weight of the composition.

3. The composition of claim 2 wherein said oil phase is a hydrocarbon oil.

4. The composition of claim 1 wherein the volatile silicone is a cyclomethicone.

5. A ringing nanogel composition comprising an oil phase, a water phase, a silicone oil component comprising at least one volatile silicone oil different than the oil phase, and less than about 8 percent by weight of the composition of an emulsifier, wherein said oil phase and said silicone component are having at least about 20 percent by weight of the composition and at least about 5 times the amount of the emulsifier self-structured in the absence of a thickening agent by a high shear/pressure treatment, and has a difference in complex viscosity of at least about 10,000 poise under oscillation stress in the range of about 0 to 5,000 (dyne/cm$^2$) and has an initial complex viscosity of greater than about 15,000 poise.

6. A method of making a ringing nanogel comprising the steps of combining an oil phase, a water phase, an emulsifier, and a silicone oil component comprising at least one volatile silicone oil different than the oil phase, to make an oil-in-water emulsion wherein the silicone component and the oil phase are at least about 20 percent by weight of the composition and are at least about 5 times the amount of the emulsifier, and subjecting the oil-in-water emulsion to a high shear/pressure treatment in the absence of a thickening agent at least two consecutive times.

7. The method of claim 6 wherein the emulsion is subjected to the high shear/pressure treatment three times.

8. The method of claim 6 wherein the ringing nanogel has a difference in complex viscosity of at least about 10,000 poise under oscillation stress in the range of about 0 to 5,000 (dyne/cm$^2$).

9. The method of claim 6 wherein the ringing nanogel has an initial complex viscosity of at least about 15,000 poise.

10. The method of claim 6 further comprising no greater than about 8 percent by weight of the composition of an emulsifier.

11. The method of claim 6 wherein the oil phase is a hydrocarbon oil.

12. The method of claim 6 wherein the volatile silicone oil is cyclomethicone.

13. A ringing nanogel composition prepared according to the method of claim 6 having less than about 8 percent by weight of the composition of an emulsifier.

* * * * *